(12) United States Patent
Tamaroff et al.

(10) Patent No.: US 7,276,905 B2
(45) Date of Patent: Oct. 2, 2007

(54) METHOD AND SYSTEM OF TRACKING AN INTRACORPOREAL DEVICE WITH MR IMAGING

(75) Inventors: Eric R. Tamaroff, Baldwin, NY (US); John Pile-Spellman, Pelham Manor, NY (US); Lei Feng, New York, NY (US); Stephen M. Dashnaw, Wayne, NJ (US); Robert L. DeLaPaz, Dobbs Ferry, NY (US)

(73) Assignees: General Electric Company, Schenectady, NY (US); The Trustees of Columbia University in the City of New York, New York, NY (US)

( * ) Notice: Subject to any disclaimer, the term of this patent is extended or adjusted under 35 U.S.C. 154(b) by 29 days.

(21) Appl. No.: 11/160,811

(22) Filed: Jul. 11, 2005

(65) Prior Publication Data

US 2007/0007957 A1    Jan. 11, 2007

(51) Int. Cl.
*G01V 3/00* (2006.01)
(52) U.S. Cl. .................................. 324/309; 600/424
(58) Field of Classification Search ............... 324/309; 600/424
See application file for complete search history.

(56) References Cited

U.S. PATENT DOCUMENTS

| | | | | |
|---|---|---|---|---|
| 5,271,400 A | * | 12/1993 | Dumoulin et al. | .......... 600/410 |
| 5,289,373 A | | 2/1994 | Zarge et al. | |
| 5,419,325 A | | 5/1995 | Dumoulin et al. | |
| 6,574,497 B1 | * | 6/2003 | Pacetti | ....................... 600/420 |
| 6,733,487 B2 | | 5/2004 | Keith et al. | |
| 6,975,896 B2 | * | 12/2005 | Ehnholm et al. | ........... 600/414 |

* cited by examiner

*Primary Examiner*—Louis M. Arana
(74) *Attorney, Agent, or Firm*—Ziolkowski Patent Solutions Group, SC (57) ABSTRACT

A system and method for tracking or otherwise determining positioning of an intracorporeal device is provided. The invention includes a device that may be inserted into a subject and tracked based on an imageable tag included with the device. The imageable tag is at least partially formed of a substance whose nuclei precess at a Larmor frequency different than the Larmor frequency of hydrogen when subjected to a polarizing magnetic field. MR data may be acquired from the imageable tag using an RF receiver tuned to the Larmor frequency of the substance and used to track movement of the device within the subject.

36 Claims, 5 Drawing Sheets

METHOD AND SYSTEM OF TRACKING AN INTRACORPOREAL DEVICE WITH MR IMAGING

BACKGROUND OF THE INVENTION

The present invention relates generally to MR imaging and, more particularly, to a method and system of imaging devices having an imageable tag that includes nuclei that precess at a Larmor frequency different than that of hydrogen when subjected to a polarizing magnetic field.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

MR imaging is frequently used for tracking or otherwise determining the position of an intracorporeal device, such as an endovascular catheter. Hereinafter, the term "intracorporeal device" generally refers to any type of device that is navigable, moveable, or otherwise insertable in whole or in part within a body. To properly guide the device, a number of tracking techniques have been developed. These techniques generally fall into one of two categories: passive tracking or active tracking.

Passive tracking utilizes signal voids or image artifacts for visualization of the medical device. Typically, the medical device is labeled with a paramagnetic marker. Paramagnetic markers are commonly used because the paramagnetic properties of the marker substance shorten its relaxation time. As such, with the appropriate pulse sequence parameters, a signal will not be collected from the marker resulting in a signal void in a reconstructed image.

Other passive tracking techniques include use of susceptibility artifacts on metal wires connected to the medical device. In this regard, the artifacts in a reconstructed image reflect the presence of the medical device. In a further passive tracking technique, electrical current is induced in the electrical wires during signal acquisition so as to modify the intensity of the artifacts for improved device detectability. Additional passive tracking techniques include use of intravascular contrast agents or the passing of similar suitable fluids through a lumen. Passive tracking of devices, however, does have drawbacks.

While passive tracking supports the simultaneous visualization of endovascular devices and subject physiology, such as blood vessels and surrounding tissue, the spatial and temporal resolutions are acquisition dependent and, as a result, the spatial and temporal resolution is inadequate to distinguish the endovascular device from subject anatomy. Further, since the markers used to tag the devices predominantly include hydrogen nuclei, it is difficult to distinguish between subject anatomy and the device with MR imaging of precessing hydrogen.

Active device tracking techniques involve the placement of an RF receiver coil on the endovascular device or use of a guide wire as a linear receiver coil. In this regard, MR signals are acquired at the endovascular device and may be used to reconstruct tracking images. While active tracking techniques are commonly preferred because of the high signal-to-noise ratio (SNR) as well as higher spatial and temporal resolution it provides, electrical wires connect the RF receiver coil to the data acquisition system of the MR scanner. These electrical wires add to the complexity of the endovascular device and can be cumbersome when inserting and positioning the device in the subject. Additionally, it may not be desirable to have electrically conductive leads extending from a subject undergoing an MR scan.

It would therefore be desirable to have a system and method capable of tracking a wireless intracorporeal device through a subject without sacrificing SNR as well as spatial and temporal resolution.

BRIEF DESCRIPTION OF THE INVENTION

The present invention provides a system and method for imaging, and in certain embodiment tracking, an intracorporeal device or any other device that may be disposed within a subject, which is tagged with an imageable marker distinguishable from the subject anatomy or an object that overcomes some or all of the aforementioned drawbacks.

A system and method for tracking or otherwise determining positioning of an intracorporeal device is provided. The invention includes a device that may be inserted into a subject and tracked based on an imageable tag included with the device. The imageable tag is at least partially formed of a substance whose nuclei precess at a Larmor frequency different than the Larmor frequency of hydrogen when subjected to a polarizing magnetic field. MR data may be acquired from the imageable tag using an RF receiver tuned to the Larmor frequency of the substance and used to track movement of the device within the subject.

Therefore, in accordance with one aspect of the present invention, a method of MR imaging is provided. The method includes impressing a polarizing magnetic field on a region-of-interest (ROI) having a device disposed therein. The device includes an imageable tag formed of at least a substance distinguishably present in the ROI and that precesses at a first Larmor frequency when subjected to the polarizing magnetic field. The method further includes subjecting the ROI to an excitation field at the first Larmor frequency and acquiring MR data from the ROI with a receiver tuned to the first Larmor frequency. The method also includes the step determining a position of the device within the ROI from the MR data.

In accordance with another aspect, the present invention includes an MRI apparatus having a magnetic resonance imaging (MRI) system that has a plurality of gradient coils positioned about a bore of a magnet to impress a polarizing magnetic field. The MRI system also has an RF transceiver system and an RF switch controlled by a pulse module to transmit RF signals to an RF coil assembly to acquire MR images from precessing hydrogen nuclei in an ROI. The MRI system further includes a computer readable storage medium having stored thereon a computer program comprising instructions, which when executed by a computer, cause the computer to cause excitation of hydrogen nuclei in the ROI. The computer is further caused to cause excitation of nuclei of at least a hydrogen-absent substance having been introduced to the ROI. Nuclei of the hydrogen-absent substance precess at a Larmor frequency different than that of hydrogen nuclei. The computer is also caused to acquire MR data from at least the ROI and reconstruct an image of the ROI that includes contrast between the substance and other structures within the ROI.

According to another aspect of the present invention, a method of MR imaging includes inserting a medical device into a subject. The medical device includes an imageable tag that precesses at a Larmor frequency different than that of hydrogen. The method further includes exciting the subject with a $B_1$ field at the Larmor frequency of hydrogen and acquiring MR data from at least nuclei in the subject precessing at the Larmor frequency of hydrogen. The method also includes reconstructing tracking images showing movement of the medical device within the subject.

In accordance with a further aspect, the present invention includes a medical device insertable into a subject. The device has a body and at least one sealed chamber connected to the body. An imageable substance including non-hydrogen nuclei is disposed in the at least one sealed chamber.

According to yet another aspect of the present invention, a medical device insertable into a subject is provided. The medical device has a body and one or more cavities formed in at least a portion of an outer surface of the tubular body. An imageable substance predominantly devoid of hydrogen at least partially fills the one or more cavities.

In accordance with yet a further aspect, a method of MR imaging includes placing a fluorinated substance into a restricted portion of a subject. A medical device is inserted into the restricted portion. The medical device is constructed substantially free of the fluorinated substance placed in the restricted portion. MR data is acquired from the restricted portion with a receiver coil at least tuned to acquire RF signals at the Larmor frequency of the fluorinated substance. The method further includes reconstructing an image of the restricted portion from the MR data and determining relative positioning of the medical device within the intracorporeal cavity from the image.

According to yet another aspect, the present invention includes a navigable MR imaging device constructed of a substance to precess at a Larmor frequency of approximately 60 MHz when subjected to an approximately 1.5 T substantially uniform magnetic field.

In accordance with yet a further aspect, the present invention includes an imaging technique having means for impressing a substantially uniform magnetic field about a subject to be imaged and means for translating a navigable device within the subject. The navigable device is constructed to have a detectable tag comprised of a substance whose nuclei precess at a Larmor frequency other than that of hydrogen nuclei. The imaging technique further has means for exciting nuclei of the substance to precess at the Larmor frequency other than that of hydrogen nuclei and means for acquiring MR data from nuclei precessing at the Larmor frequency other than that of hydrogen nuclei. Means for actively tracking displacement of the navigable device within the subject is also provided.

Various other features, objects, and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
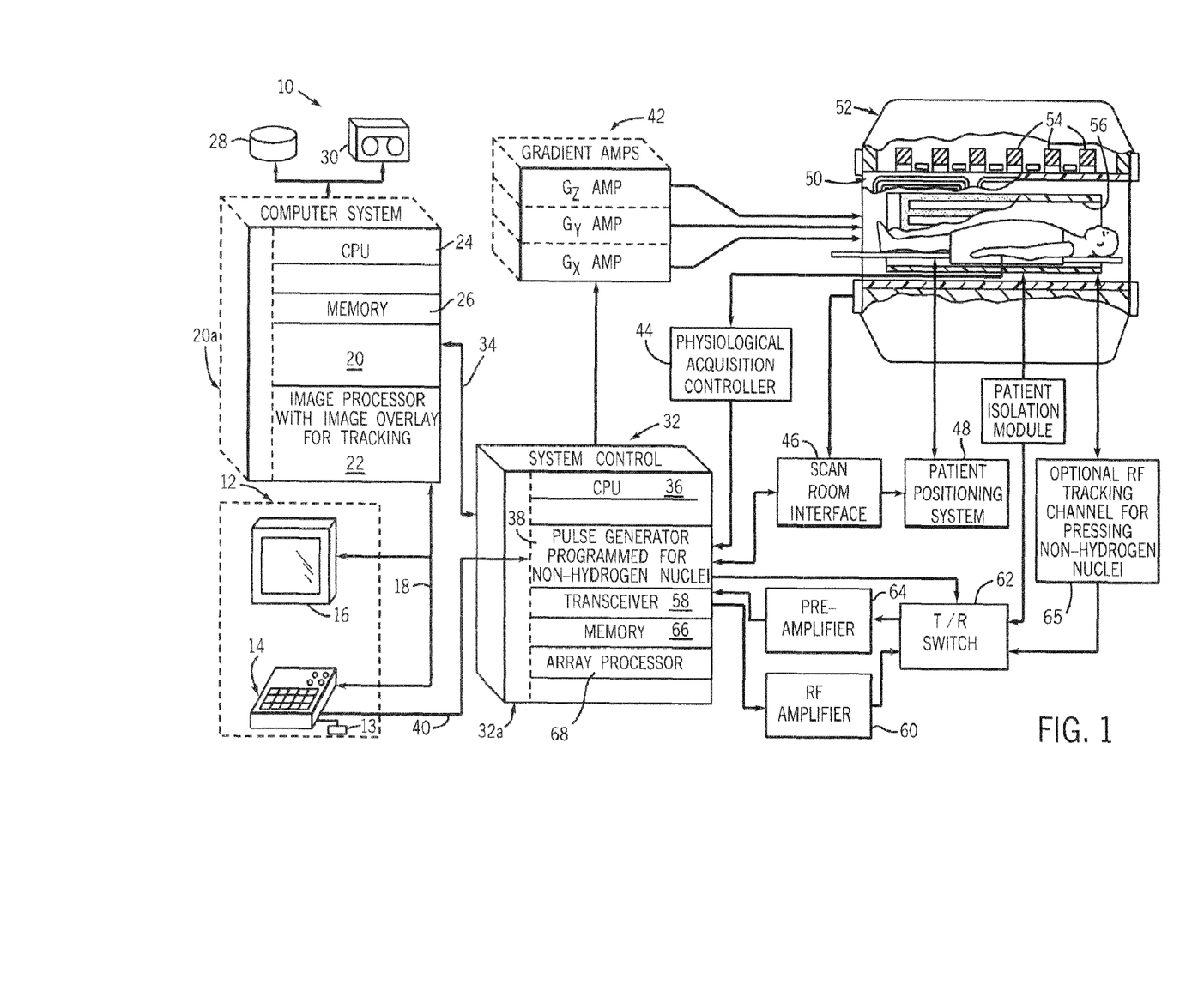
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a system controller 32 through a high speed serial link 34. The input device 13 can include a mouse, joystick, keyboard, track ball, touch activated screen, light wand, voice control, or any similar or equivalent input device, and may be used for interactive geometry prescription.

The system controller 32 includes a set of modules connected together by a backplane 32a. These include a CPU module 36 and a pulse generator module 38 which connects to the operator console 12 through a serial link 40. It is through link 40 that the system controller 32 receives commands from the operator to indicate the scan sequence that is to be performed. The pulse generator module 38 programmed to operate the system components to carry out the desired scan sequence and produces data which indicates the timing, strength and shape of the RF pulses produced, and the timing and length of the data acquisition window for precessing non-hydrogen nuclei and imaging devices having a substance distinguishably present in a region of interest as discussed herein. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system controller 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either a transmit or receive mode. The system may further include an optional RF tracking channel 65 configured for precessing non-hydrogen nuclei and a patient isolation module 63 for isolating image data for the sight of interest from that of the device as described herein.

The MR signals picked up by the RF coil 56 are digitized by the transceiver module 58 and transferred to a memory module 66 in the system controller 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16. The image processor 22 may further be adapted, e.g., with software, hardware, or a combination thereof, to overlay a reconstructed image of the device from MR data over a reconstructed image of the sight of interest.

As will be described more fully below, RF coil 56 may be tuned to pick up MR signals at more than one frequency. For instance, the coil 56 may be tuned to pick up MR signals precessing at the Larmor frequency of hydrogen nuclei as well as the Larmor frequency of non-hydrogen nuclei, such as carbon, fluorine, sodium, phosphorus, and oxygen. Moreover, the coil 56, in one embodiment, may be constructed to pick up signals from precessing hydrogen nuclei and a precessing given non-hydrogen nuclei simultaneously. In a further embodiment, the RF coil may be constructed to have a reception bandwidth that includes the precessing frequency of hydrogen nuclei and a given non-hydrogen nuclei. The precessing frequency is, in part, a function of the strength of the polarizing magnetic field to which the nuclei are subjected. As such, the RF coil is tuned to the appropriate precessing frequencies depending upon whether the MR scanner is designed to impress a substantially uniform 1.5 Tesla magnetic field or other field strength. Additionally, the MR scanner may be constructed to have more than one RF coil for MR signal reception. In this embodiment, one RF coil is tuned to receive MR signal from precessing hydrogen nuclei whereas another RF coil is tuned to receive MR signals from precessing non-hydrogen nuclei, such as fluorine, sodium, carbon, phosphorus, oxygen, heavy water, and the like. The Larmor frequency of hydrogen nuclei in a 1.5 Tesla magnetic field is about 63.5 MHz and the Larmor frequency of fluorine in the same magnetic field is about 60.08 MHz.

In one embodiment, the present invention is directed to the acquisition of MR signals from precessing non-hydrogen nuclei. In another embodiment, the present invention is directed to the simultaneous or near simultaneous acquisition of MR signals from precessing hydrogen nuclei and precessing non-hydrogen nuclei. In this regard, the MR scanner is capable of creating a $B_1$ field at the Larmor frequency of hydrogen as well as at the Larmor frequency of a given non-hydrogen nuclei, such as fluorine, sodium, carbon, phosphorus, and oxygen. Generally, nuclei with an atomic number less than twenty may be targeted for signal acquisition. In addition to non-hydrogen nuclei, it is contemplated that enriched hydrogen compounds, such as deuterium enriched water (heavy water), and compounds having hyperpolarized hydrogen (hyperpolarized water) may also be targeted for signal acquisition.

Figure 2:
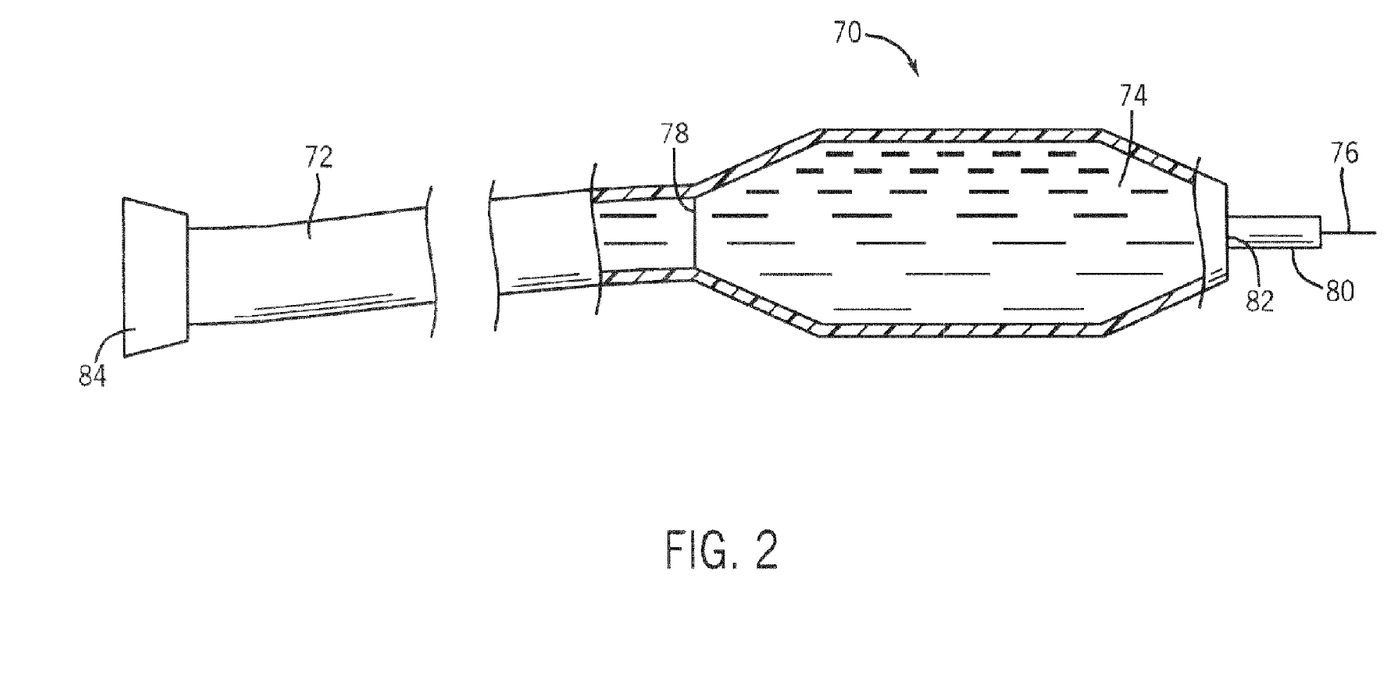
FIG. 2 is a perspective view of an intracorporeal device according to one embodiment of the invention usable with an MR imaging system.

Referring now to FIG. 2, an endovascular catheter 70 is shown in perspective. While the invention will be described with respect to a balloon dilatation catheter, one skilled in the art will readily appreciate that the present invention is applicable with other intracorporeal devices, such as general purpose and special purpose catheters, biopsy needles, laparoscopes, endoscopes, and other surgical tools, stents, shunts, and other implantable devices, pills, particles, liquids, gases, and other injectable, ingestible, or inhale-able agents, as well as non-intracorporeal devices, and is thus not limited thereto. Catheter 70 has a shaft section 72 with a balloon section 74 generally disposed near its distal end 76. Shaft section 72 is connected or otherwise integrally formed with the proximal end 78 of balloon section 74. A distal waist section 80 is connected or otherwise formed between a distal end 82 of the balloon section 74 and the distal end 76 of the catheter 70.

The lumen or bore of the catheter 70 is designed to allow the passage of fluid or other inflating solution from a fluid source (not shown) connected to a proximal end 84 to the balloon section 74. A pump or other inflation device (not shown) may also be connected to the catheter to control the inflation and deflation of balloon section 74. The catheter, which may be widely used in angiographic procedures, may also be used to position an endovascular RF coil within proximity of a target tissue or in the vasculature for blood imaging. In this regard, an RF coil may be translated through the catheter once the catheter has been properly positioned within the vasculature. The advantages of which will be described in greater detail below, the RF coil is translated through the catheter after the catheter has been positioned and, as such, the RF coil assembly does not restrict movement or hinder positioning of the catheter during translation through the subject.

Visualization of catheter 70 is achieved by determining the position of the catheter 70 in relation to the ROI through MR imaging of the subject. Tracking is similarly achieved through sequential generation of MR images, which assists the physician or other health care professional in translating the catheter through the subject vasculature or other anatomy. To provide contrast between the catheter and the subject anatomy, in one embodiment, a pump (not shown) delivers a compound or other substance to the catheter that is distinguishably present in the subject anatomy, e.g., because the compound is not prevalently found, is minimally present, or is otherwise present in distinguishable concentrations or forms in the subject anatomy or in the particular ROI, e.g., fluorine or fluorinated compounds, or any other applicable non-hydrogen nuclei substances. In this regard, the MR scanner can either carry out a hydrogen-based MR scan whereupon MR signals are acquired from precessing hydrogen nuclei, or carry out an MR scan whereupon precessing non-hydrogen nuclei are the subject of signal acquisition. Hydrogen is typically the nuclei from which MR signals are acquired because of its abundance in the subject anatomy. Fluorine, on the other hand, is distinguishable from the subject anatomy since it is minimally found in the subject anatomy and is particularly limited to bones and teeth. Moreover, in its crystal form, fluorine is immobile and therefore has a relaxation time that is too short to be readily detectable when using imaging methods sensitive to freely mobile liquid forms of fluorinated compounds, such as hexafluorobenzene. Accordingly, when the catheter is at least partially filled with fluorine or a fluorinated compound, the low level (or non-existent) fluorine background signal allows for improved visualization of the fluorine-filled catheter in a reconstructed image constructed from MR data acquired from precessing fluorine nuclei. As a result, the fluorine labeled intracorporeal device may be detected with higher spatial and temporal resolution, such as spatial resolution less than 0.5 millimeters (mm) and temporal resolution less than 0.1 second. Experimentally, crisp images of a 1.5 F catheter (less than 0.5 mm in diameter) filled with fluorinated fluid have been generated.

It is contemplated that a number of fluorinated fluids may be delivered to the catheter to label the catheter. As mentioned above, hexafluorobenzene is one such compound that may be used. Perfluorocarbon is another contemplated compound. Known perfluorocarbon solutions contain approximately ten to twenty fluorine moieties per molecule and are devoid of hydrogen, thus making perfluorocarbon labeled devices highly visible with fluorine tuned RF receivers or coils. Perfluorocarbon is widely regarded as a synthetic substitute for blood and, as such, can provide information about local blood flow, oxygen levels and temperature. That is, changes in fluorine $T_1$ and $T_2$ relaxation times vary directly with oxygen tension. These relaxation times are generally shorter at higher oxygen levels in the physiological range. Temperature also affects the relaxation times of perfluorocarbons. Rising temperatures will increase the $T_1$ relaxation time and decrease the $T_2$ relaxation time.

Alternative compounds, such as those containing sodium, may also be used. Sodium beneficially precesses at a frequency of about half to one-third that of hydrogen, which provides an improved signal to noise ratio. Precessing sodium also produces a distinguishable signal from hydrogen and is relatively non-toxic.

As described above, a fluorinated fluid may be delivered to and through the lumen of the intracorporeal device and used to label the device for subsequent visualization in a reconstructed image. If MR signals are acquired from precessing fluorine, then the device will appear stark in the image and if MR signals are acquired from precessing hydrogen, the device will appear as a signal void in the reconstructed image. It is contemplated however that the device may be tagged in other ways. For example and referring to FIG. 3, a cross-sectional view of the generally distal end of catheter 70 according to another embodiment of the invention is shown. In this embodiment, a sealed cylinder 86 having a fluorinated compound 87 therein is shown circumferentially around distal waist section 80. Cylinder 86 may be permanently secured to waist section 80 or resiliently secured to allow replacement with other cylinders having other non- or limited hydrogen contents or different degrees of fluorine. While a cylinder 86 that is snuggly secured to the catheter is shown, it is contemplated that other sealed fluorinated structures may be connected or otherwise formed with the catheter. It is recognized that cylinder 86 should be secured to the catheter in such a fashion so as to prevent disconnection of the cylinder from the catheter during translation of the catheter in the subject. Relatively non-toxic compounds containing, e.g., sodium nuclei, may also be incorporated into the device without the need for a sealed structure, e.g., with a coating containing the applicable substance.

Figure 3:
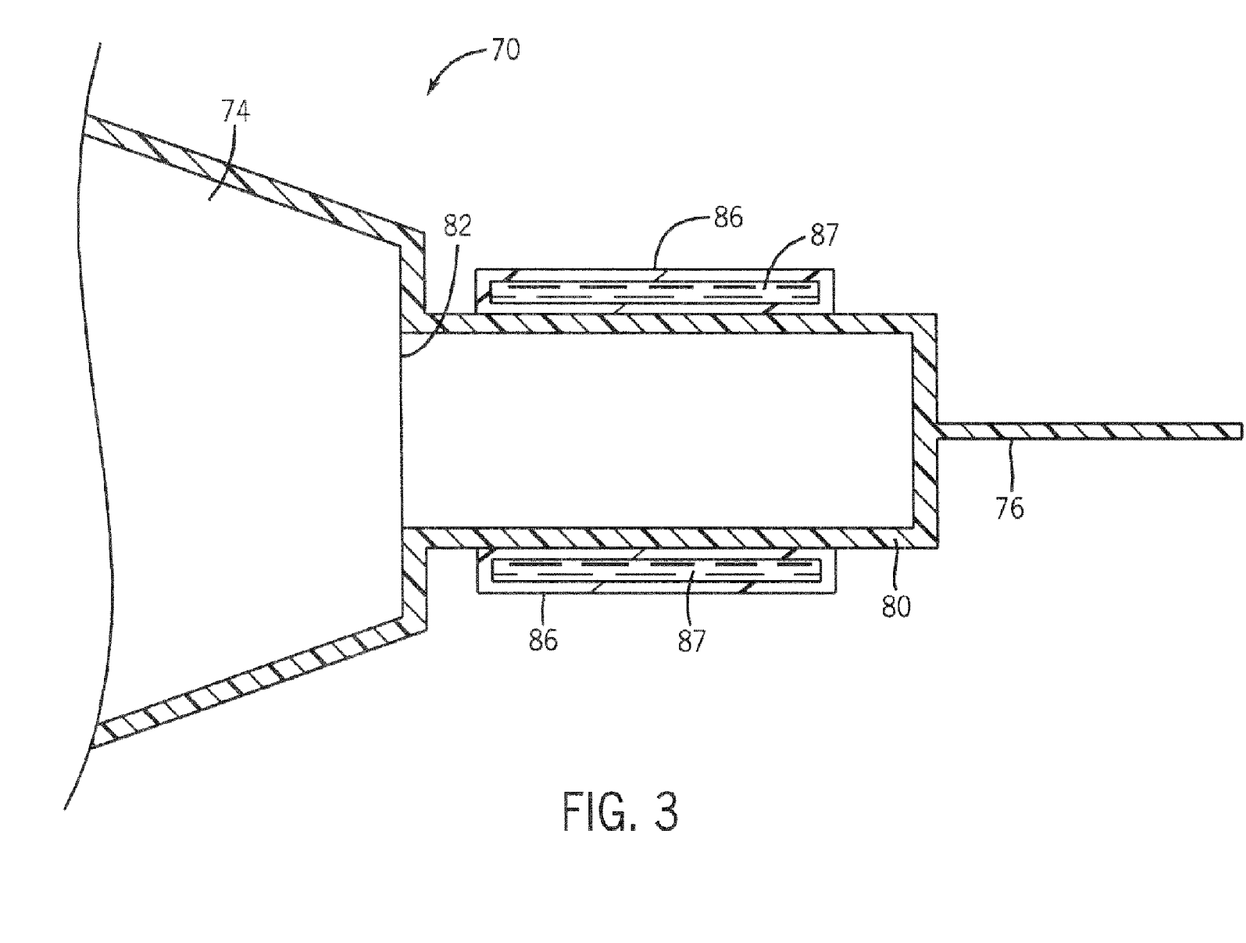
FIG. 3 is a partial cross-sectional view of an intracorporeal device according to another embodiment of the invention.

As mentioned above, cylinder 86 is a sealed structure containing a fluorinated compound or other solution 87. Similar to flooding the lumen with such a solution, the catheter labeled with cylinder 86 may be readily visualized with either fluorine based or hydrogen based scan. It is also contemplated that more than one sealed structure may be connected or otherwise integrated with the catheter so that movement or translation of more than one portion of the catheter may be tracked.

Figure 4:
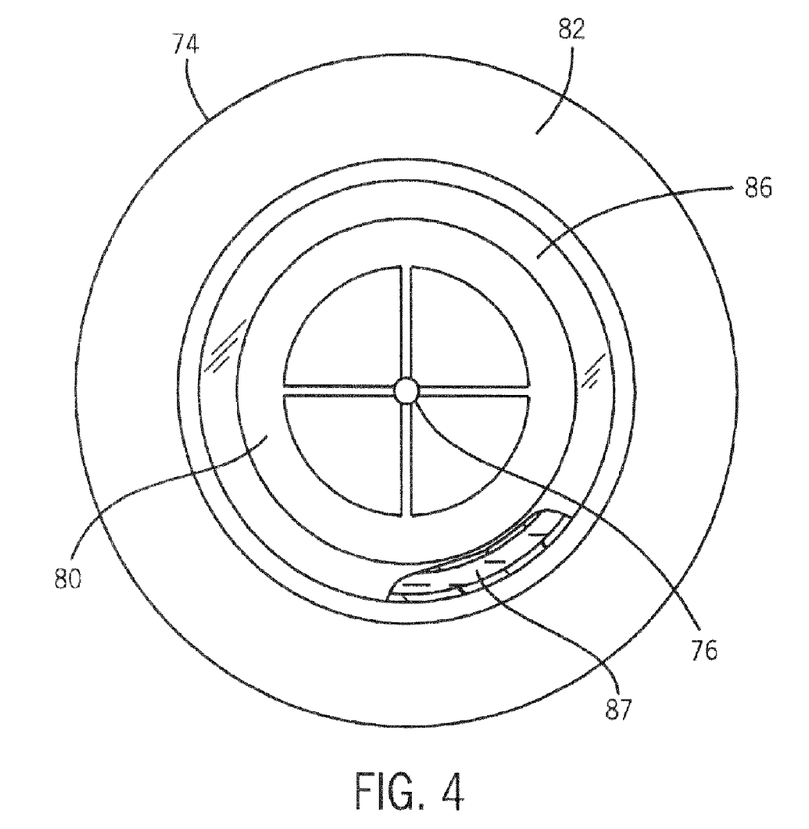
FIG. 4 is an end view of an intracorporeal device according to one embodiment of the invention.

Referring now to FIG. 4, an end view of the device shown in FIG. 3 illustrates the concentric relationship between the distal waist section 80 and the sealed cylinder 86. Further illustrated in FIG. 4 is the hollowed nature of the catheter components except for the sealed cylinder 86 which is filled with a fluorinated compound or other non-hydrogen or minimally hydrogen-containing substance. It should be noted that the relative size of the sealed cylinder 86 compared to that of the structural elements of the catheter is for illustrative purposes only and that it is contemplated that cylinders with larger or smaller diameters may be used.

Figure 5:
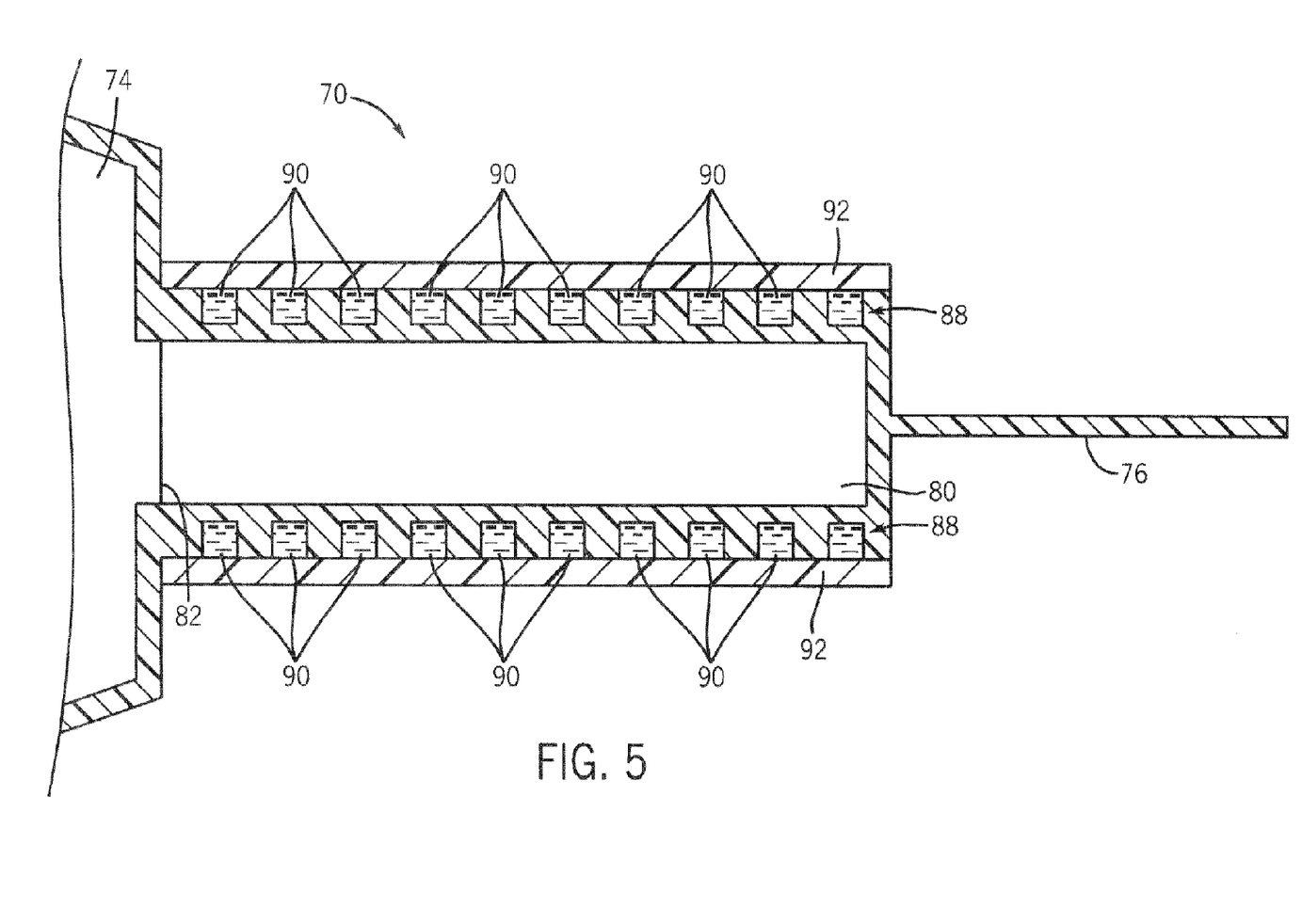
FIG. 5 is a partial cross-sectional view of an intracorporeal device according to another embodiment of the present invention.

Referring now to FIG. 5, a cross-sectional view of the generally distal end of catheter 70 in another embodiment illustrates that the distal waist 80 may be constructed with a porous surface 88. The pores of the porous surface may then be at least partially filled with a fluorinated solution 90 and sealed within the pores with a non-soluble sealant or coating 92.

Heretofore the present invention has been described with respect to the direct labeling of an intracorporeal device with a fluorinated fluid. However, the present invention is also directed to the indirect labeling of such a device. In this embodiment, a cavity within a subject may be at least partially filled with a fluorinated fluid, such as perfluorocarbon. As a result, when a standard intracorporeal device, devoid of or minimally containing fluorine or another non-hydrogen element, is placed within the cavity, the device will appear as a conspicuous signal void in the reconstructed image of MR data acquired from presessing fluorine or other non-hydrogen nuclei. Conversely, with the acquisition of MR data from precessing hydrogen nuclei, the device would be detectable on a background devoid of signal.

As referenced above, the SNR of a fluorine label is very high when acquiring MR signals from precessing fluorine nuclei. As such, the fluorine label can be rapidly localized three-dimensionally. Further, the coordinates of the fluorine label can be used to orientate the imaging plane to the medical device to support improved imaging of the device and the surrounding physiology.

Additionally, the present invention is also directed to the sequential as well as essentially simultaneous acquisition of MR signals from precessing fluorine nuclei and hydrogen nuclei. In this regard, separate images may be constructed and then superimposed over one another on a single display.

As a result, the precessing hydrogen nuclei provide resolution of the subject anatomy and the precessing fluorine nuclei provide resolution of the intracorporeal device.

Heretofore the present invention has been described with respect to the acquisition of MR signals from precessing fluorine nuclei in addition to the acquisition of MR signals from precessing hydrogen nuclei. However, one skilled in the art will appreciate that other non-hydrogen nuclei may be targeted. For example, in addition to fluorine, isotopes of carbon, sodium, phosphorus, and oxygen nuclei may be targeted. In addition, noble gases may be added to the device tag to alter the relaxation times of the tag. In this regard, different labels of the same base content but with varying degrees of noble gases may be used to differentiate between labels and/or devices.

The present invention provides a device tracking method and system that provides spatial and temporal resolution on par with that heretofore achieved only with active tracking techniques, but avoids the electrical leads typically required of an active tracking coil. In this regard, the present invention provides for a wireless intracorporeal device and wireless tracking method that allows the device to be automatically detected by its relatively high conspicuity with fluorine or other non-hydrogen imaging. Moreover, the present invention may be used to orient standard proton imaging planes to visualize surrounding tissue.

A method of MR imaging is provided. The method includes impressing a polarizing magnetic field on a region-of-interest (ROI) having an intracorporeal device disposed therein. The intracorporeal device includes an imageable tag formed of at least a substance minimally present in the ROI and that precesses at a first Larmor frequency when subjected to the polarizing magnetic field. The method further includes subjecting the ROI to an excitation field at the first Larmor frequency and repeatedly acquiring MR data from the ROI with a receiver tuned to the first Larmor frequency. The method also includes the step of tracking movement of the intracorporeal device within the ROI from the MR data.

The present invention also includes an MRI apparatus having a magnetic resonance imaging (MRI) system that has a plurality of gradient coils positioned about a bore of a magnet to impress a polarizing magnetic field. The MRI system also has an RF transceiver system and an RF switch controlled by a pulse module to transmit RF signals to an RF coil assembly to acquire MR images from precessing hydrogen nuclei in an ROI. The MRI system further includes a computer readable storage medium having stored thereon a computer program comprising instructions, which when executed by a computer, cause the computer to cause excitation of hydrogen nuclei in the ROI. The computer is further caused to cause excitation of nuclei of at least a hydrogen-absent substance having been introduced to the ROI. Nuclei of the hydrogen-absent substance precess at a Larmor frequency different than that of hydrogen nuclei. The computer is also caused to acquire MR data from at least the ROI and reconstruct an image of the ROI that includes contrast between the substance and other structures within the ROI.

A method of MR imaging is disclosed and includes inserting a medical device into a subject. The medical device includes an imageable tag that precesses at a Larmor frequency different than that of hydrogen. The method further includes exciting the subject with a $B_1$ field at the Larmor frequency of hydrogen and acquiring MR data from at least nuclei in the subject precessing at the Larmor frequency of hydrogen. The method also includes repeatedly reconstructing tracking images showing movement of the medical device within the subject.

The present invention also includes a medical device insertable into a subject. The device has an encapsulated body and at least one sealed chamber connected to the tubular body. An imageable substance including non-hydrogen nuclei is disposed in the at least one sealed chamber.

A medical device insertable into a subject is provided. The medical device has a body and one or more cavities formed in at least a portion of an outer surface of the tubular body. An imageable substance predominantly devoid of hydrogen at least partially fills the one or more cavities.

A method of MR imaging is disclosed and includes placing a fluorinated substance into a restricted portion of a subject. A medical device is inserted into the restricted portion. The medical device is constructed substantially free of the fluorinated substance placed in the restricted portion. MR data is acquired from the restricted portion with a receiver coil at least tuned to acquire RF signals at the Larmor frequency of the fluorinated substance. The method further includes reconstructing an image of the restricted portion from the MR data and determining relative positioning of the medical device within the intracorporeal cavity from the image.

The present invention is further directed to a navigable MR imaging device constructed of a substance to precess at a Larmor frequency of approximately 60 MHz when subjected to an approximately 1.5 T substantially uniform magnetic field.

An imaging technique is provided and is defined as having means for impressing a substantially uniform magnetic field about a subject to be imaged and means for translating a navigable device within the subject. The navigable device is constructed to have a detectable tag comprised of a substance whose nuclei precess at a Larmor frequency other than that of hydrogen nuclei. The imaging technique further has means for exciting nuclei of the substance to precess at the Larmor frequency other than that of hydrogen nuclei and means for acquiring MR data from nuclei precessing at the Larmor frequency other than that of hydrogen nuclei. Means for actively tracking displacement of the navigable device within the subject is also provided.

The present invention has been described in terms of the preferred embodiment, and it is recognized that equivalents, alternatives, and modifications, aside from those expressly stated, are possible and within the scope of the appending claims.

What is claimed is:

1. A method of MR imaging comprising the steps of:
   impressing a polarizing magnetic field on an ROI having a device disposed therein, the device comprising an imageable tag formed at least of a substance distinguishably present in the ROI and that precesses at a first Larmor frequency when subjected to the polarizing magnetic field;
   subjecting the ROI to an excitation filed at the first Larmor frequency;
   acquiring MR data from the ROI with a receiver tuned to the first Larmor frequency;
   reconstructing an image of the ROI from the acquired MR data; and
   determining a position of the device within the ROI from the reconstructed image.

2. The method of claim 1 further comprising the step of refreshing the image with a second acquisition of MR data to localize position of the device within the ROI.

3. The method of claim 1 wherein the first Larmor frequency is different than that of precessing hydrogen.

4. The method of claim 1 further comprising the step of acquiring a first set of MR data from the ROI at the first Larmor frequency and acquiring a second set of MR data from precessing hydrogen in the ROI at a second Larmor frequency different from the first Larmor frequency.

5. The method of claim 4 further comprising the step of acquiring the sets of MR data from the ROI at the first and second Larmor frequencies with a dual-tuned RF receiver.

6. The method of claim 5 wherein the dual-tuned RF receiver is capable of receiving RF signals at about 63.5 MHz and at about 60.08 MHz at 1.5T.

7. The method of claim 4 further comprising the step of acquiring the sets of MR data from the ROI at the first and second Larmor frequencies with a single RF receiver having a frequency reception bandwidth comprising one of about 63.5 MHz and about 60.08 MHz at 1.5T.

8. The method of claim 4 further comprising the steps of reconstructing a first image from the first set of MR data and a second image from the second set of MR data and superimposing the first and second images onto one another.

9. The method of claim 4 further comprising the step of acquiring the first set and the second set of MR data essentially simultaneously.

10. The method of claim 4 further comprising the steps of acquiring the first set of MR data with one or more RF coils tuned to the Larmor frequency of isotopes of one of fluorine, phosphorus, carbon, and sodium and acquiring the second set of MR data with one or more coils tuned to the Larmor frequency of a hydrogen isotope.

11. The method of claim 1 wherein the substance is fluorine-based.

12. The method of claim 11 wherein the fluorine-based substance comprises one of perfluorocarbon and hexafluorobenzene.

13. The method of claim 1 further comprising the step of determining at least one of blood flow, oxygen tension, and temperature through the device.

14. The method of claim 1 further comprising the steps of:
subjecting the ROI to an excitation field at a second Larmor frequency different from the first Larmor frequency;
acquiring MR data from the ROI with a receiver tuned to at least the second Larmor frequency; and
determining a position of a second device within the ROI, the second device comprising an imageable tag formed at least partially of a second substance that precesses at the second Larmor frequency when subjected to the polarizing magnetic field.

15. The method of claim 14 further comprising the step of reconstructing an image that includes contrast differentiation between anatomical make-up of the ROI, the first device, and the second device.

16. An MRI apparatus comprising:
a magnetic resonance imaging (MRI) system having a plurality of gradient coils positioned about a bore of a magnet to impress a polarizing magnetic field;
an RF transceiver system and an RF switch controlled by a pulse module to transmit RF signals to an RF coil assembly to acquire MR images from precessing nuclei in an ROI; and
a computer readable storage medium having stored thereon a computer program comprising instructions which when executed by a computer causes the computer to:
cause excitation of hydrogen nuclei in the ROI;
cause excitation of nuclei of at least a hydrogen-absent substance having been introduced to the ROI, the nuclei of the hydrogen-absent substance designed to precess at a Larmor frequency different than that of hydrogen nuclei;
acquire a first set of MR data from precessing hydrogen nuclei;
acquire a second set of MR data from precessing non-hydrogen nuclei; and
reconstruct an image from each of the first and second sets of MR data.

17. The MRI apparatus of claim 16 wherein the hydrogen-absent substance is predominately comprised of fluorine.

18. The MRI apparatus of claim 17 wherein the hydrogen-absent substance comprises one of perfluorocarbon and hexafluorobenzene.

19. The MRI apparatus of claim 17 wherein the hydrogen-absent substance has 10-20 fluorine moieties per molecule.

20. The MRI apparatus of claim 16 wherein the hydrogen-absent substance is housed within a sealed chamber of an intracorporeal device, and wherein the computer is further caused to repeatedly reconstruct images of the ROI showing relative movement of the intracorporeal device within the ROI.

21. The MRI apparatus of claim 20 wherein the intracorporeal device comprises a catheter.

22. The MRI apparatus of claim 16 wherein the substance comprises isotopes of one of fluorine, phosphorus, carbon, and sodium.

23. The MRI apparatus of claim 16 further comprising a single RF receiver configured to receive MR signals from precessing hydrogen nuclei and a given precessing non-hydrogen nuclei.

24. The MRI apparatus of claim 23 wherein the single RF receiver is tuned to acquire RF signals essentially simultaneously from precessing hydrogen nuclei and precessing non-hydrogen nuclei.

25. The MRI apparatus of claim 16 wherein the computer is further caused to display a superimposed image of the reconstructed images over one another.

26. A method of MR imaging comprising the steps of:
inserting a medical device into a subject, the medical device comprising an imageable tag that precesses at a Larmor frequency different than that of hydrogen;
exciting the subject with a B1 field at the Larmor frequency different than that of hydrogen;
essentially simultaneously acquiring MR data from at least nuclei in the subject precessing at the Larmor frequency of hydrogen and precessing at the Larmor frequency different than that of hydrogen; and
reconstructing tracking images showing movement of the medical device within the subject.

27. The method of claim 26 further comprising the step of reconstructing comprises reconstruction a tracking image of the essentially simultaneously acquired MR data.

28. The method of claim 27 further comprising the step of essentially simultaneously acquiring MR data comprises essentially simultaneously acquiring MR data from precessing hydrogen nuclei and at least one of precessing fluorine, carbon, phosphorus, and sodium nuclei.

29. The method of claim 26 wherein the imageable tag comprises a sealable chamber at least partially filling the sealable chamber with a fluid devoid of hydrogen.

30. The method of claim 29 wherein the fluid comprises one of perfluorocarbon and hexafluorobenzene.

31. The method of claim 26 wherein the medical device comprises a catheter, and the method further comprising the step of passing a fluid devoid of hydrogen through the catheter.

32. The method of claim 26 wherein the medical device comprises a porous surface defining a number of cavities sealingly filled with a composition devoid of hydrogen.

33. A method of MR imaging comprising the steps of:
placing a fluorinated substance into a restricted portion of a subject;
inserting a medical device into the restricted portion and into the fluorinated substance, the medical device constructed substantially free of the fluorinated substance placed in the restricted portion;
acquiring MR data from the restricted portion with a receiver coil at least tuned to acquire RF signals at a Larmor frequency of the fluorinated substance; and
reconstructing an image of the restricted portion from the MR data.

34. The method of claim 33 further comprising the step of determining a relative position of the medical device within the restricted portion from the image.

35. An imaging technique comprising:
means for impressing a substantially uniform magnetic field about a subject to be imaged;
means for translating a navigable device within the subject, the navigable device having a detectable tag comprised of a substance having nuclei that precess at a Larmor frequency other than that of hydrogen nuclei;
means for exciting nuclei of the substance to precess at the Larmor frequency of hydrogen nuclei;
means for exciting nuclei of the substance to precess at the Larmor frequency other than that of hydrogen nuclei;
means for essentially simultaneously acquiring MR data from nuclei precessing at the Larmor frequency of hydrogen nuclei and from nuclei precessing at the Larmor frequency other than that of hydrogen nuclei;
means for actively tracking displacement of the navigable device within the subject.

36. The imaging technique of claim 35, further comprising means for reconstructing an image from the essentially simultaneously acquired MR data.

* * * * *

UNITED STATES PATENT AND TRADEMARK OFFICE
CERTIFICATE OF CORRECTION

PATENT NO. : 7,276,905 B2  Page 1 of 1
APPLICATION NO. : 11/160811
DATED : October 2, 2007
INVENTOR(S) : Tamaroff et al.

It is certified that error appears in the above-identified patent and that said Letters Patent is hereby corrected as shown below:

Col. 12, insert before line 43, (Claim 26), -- exciting the subject with a B1 field at the Larmor frequency of hydrogen; --.

Col. 12, line 51 (Claim 27), delete "further comprising" and substitute therefore -- wherein --.

Col. 12, lines 54 (Claim 28), delete "further comprising" and substitute therefore -- wherein --.

Signed and Sealed this

Twenty-fifth Day of December, 2007

JON W. DUDAS
*Director of the United States Patent and Trademark Office*